US00PP17194P2

(12) United States Plant Patent
Korlipara

(10) Patent No.: US PP17,194 P2
(45) Date of Patent: Nov. 7, 2006

(54) ***ECHINACEA PURPUREA* PLANT NAMED 'HOPE'**

(50) Latin Name: *Echinacea purpurea*
Varietal Denomination: Hope

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 38 days.

(21) Appl. No.: 11/154,782

(22) Filed: Jun. 15, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct cultivar of *Echinacea purpurea* plant named 'Hope' characterized by its unique flowers with soft pink ray florets that are spread out perpendicular to the stem, orange disc, lovely fragrance, and an upright vigorous habit.

1 Drawing Sheet

Botanical denomination: *Echinacea purpurea.*
Variety designation: 'Hope'.

The present invention relates to a new and distinct cultivar of *Echinacea purpurea* and given the name 'Hope'. *Echinacea* is in the family Asteraceae. This new cultivar originated as a mutation of a tetraploid selection of *Echinacea* 'Ruby Giant' (a non introduced, proprietary, unpatented plant). The mutation was induced using colchicine.

This new *Echinacea purpurea* cultivar is distinguished by:

1. Large soft pink flowers with a double row of ray florets.
2. Ray florets spread out stiffly, parallel to ground.
3. Orange cones.
4. Lovely fragrance.
5. Strong upright stems.
6. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a close up of the flowers of a one year old *Echinacea purpurea* 'Hope' growing in the ground in the field in the summer in Canby, Oreg.

DETAILED PLANT DESCRIPTION

The following is a detailed description of the new *Echinacea purpurea* cultivar based on observations of a one-year-old specimen growing in the ground in full sun under typical outdoor conditions Canby is Zone 8 on the USDA Hardiness map. Temperatures range from a high of 95 degrees F. in August to 32 degrees F. in January. Normal rainfall in Canby is 42.8 inches per year in the trial fields in Canby, Oreg. The color descriptions are all based on The Royal Horticultural Society Colour Chart.

Botanical denomination: *Echinacea purpurea.*
Variety designation: 'Hope'.

Plant:
- *Type.*—Herbaceous perennial.
- *Hardiness.*—USDA Zones 4 to 9.
- *Size.*—30 cm wide and 78 cm tall to top of flowers.
- *Form.*—Basal clump.
- *Vigor.*—Excellent.
- *Roots.*—Fibrous, with many downward growing and few laterals, ivory in color, Yellow White 158D. Roots develop easily from cuttings from the crown.

Stem:
- *Type.*—Ascending.
- *Size.*—50 cm tall to top of flowers and 9 mm wide.
- *Internode length.*—5 to 7 cm.
- *Surface texture.*—Strigose.
- *Color.*—Yellow Green 145A on shaded side and Greyed Purple 187A to B on sun side.

Leaf:
- *Type.*—Simple.
- *Shape.*—Ovate.
- *Arrangement.*—Alternate.
- *Blade length.*—8 to 15 cm.
- *Width.*—4.5 to 6 cm at the widest part.
- *Margins.*—Serrate.
- *Apex.*—Acuminate.
- *Base.*—Attenuate, continuing down petiole.
- *Surface texture.*—Strigose.
- *Venation.*—Pinnate, with three main veins from near the base.
- *Color.*—Topside — Deep Green, Closest to Yellow Green 147A, but darker. Bottom — Yellow Green 147B.
- *Petiole size.*—12.5 cm if basal leaf, 0 to 2 cm if cauline leaf and 4 mm wide on both.
- *Petiole surface texture.*—Strigose.
- *Petiole color.*—Yellow Green 147B overall.

Inflorescence:

*Type.*—Long stalked terminal heads.

*Peduncle.*—Height: 7.5 cm. Diameter: 8 mm near flower head. Surface texture: Strigose. Color: Yellow Green 145A speckled or mottled with Greyed Orange 174A.

Flower:

*Type.*—Perfect, zygomorphic.

*Size.*—11.5 cm wide and 2 to 4 cm deep as disc enlarges.

*Ray florets.*—In 2 series with prominent pleats or veins. Shape: Oblanceolate with the tip two to three toothed, margin entire, tip acute. Size: grows to 5 cm long, 1.3 cm wide. Texture: Rubbery. Surface texture: Glabrous. Color: Ray floret, topside — Red Purple 65C with 65A at base. Ray floret, bottom side — Red Purple 65A.

*Disc.*—Shape: Convex becoming conic. Size: 5.5 cm wide and becoming 3.5 cm deep with maturity. Color: Yellow Green 144B when in bud, opening to orange, Yellow Orange 28A overall.

*Disc floret.*—12 mm long, Yellow Green 144B, 5 lobed, each disc floret with one persistent, very stiff bract, 16 mm long, which gives the disc color. Bract color: Yellow Green 144B when in bud, changing to orange, Orange 24A and B tipped with Greyed Red 182A to Greyed Purple 187A at the very tip.

*Pistil.*—6 mm long, extruding, 2-branched stigma, Greyed Purple 187C.

*Stamen.*—5 in number.

*Pollen color.*—Male sterile.

*Phyllaries.*—Phyllaries in four leafy series, lobes lanceolate in shape, reflexed, strigose, area 5 cm wide.

*Phyllary size.*—Grows to 22 mm long and 5 mm wide.

*Phyllary color.*—Yellow Green 147A.

*Bloom period.*—July through September in Canby, Oreg.

*Fragrance.*—Lovely, strong.

Seed: Not Seen.

*Fertility.*—Fertile.

Disease and pests: *Echinacea* are susceptible to leaf miners, powdery mildew, bacterial spots, and gray mold. None of these have been observed on plants grown under commercial conditions in Canby, Oreg.

COMPARISONS TO SIMILAR *ECHINACEA*

Compared to *Echinacea purpurea* 'Ruby Giant' and 'Magnus', both unpatented plants, the flowers of this new cultivar are pale purplish pink rather than red purple. The parent, *Echinacea purpurea* 'Ruby Giant' tetraploid, looked the same as the diploid form of *Echinacea purpurea* 'Ruby Giant', except the leaves, flowers, and stems had more substance.

I claim:

1. A new and distinct cultivar of *Echinacea purpurea* plant as illustrated and described.

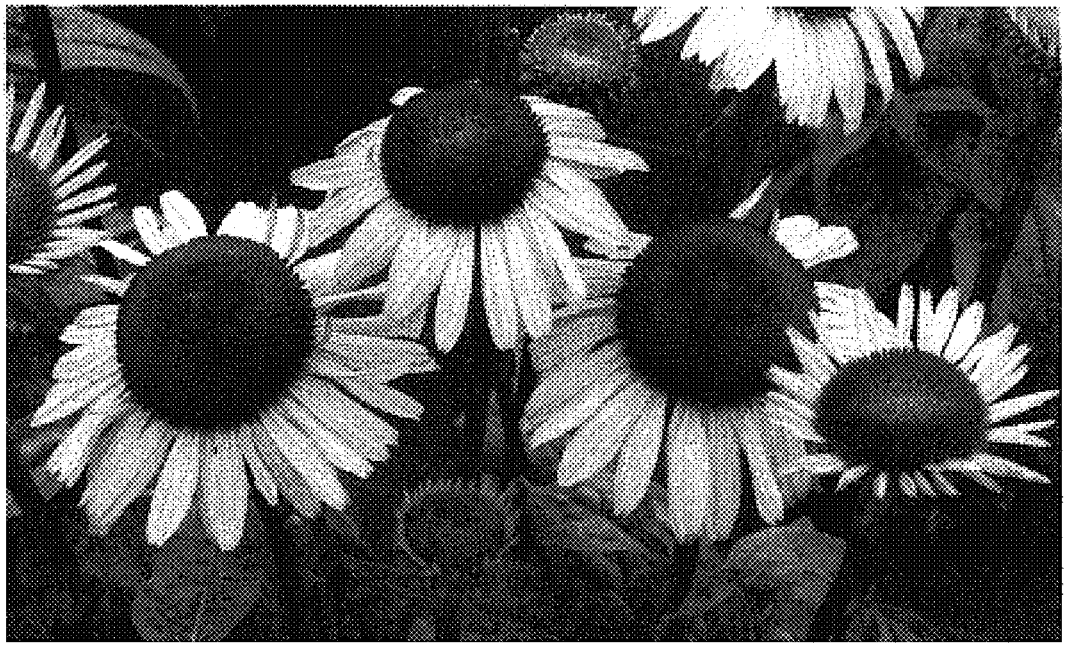

* * * * *